(12) United States Patent
Carmichael et al.

(10) Patent No.: US 6,869,282 B2
(45) Date of Patent: Mar. 22, 2005

(54) IMPLANT POSITIONING DEVICE AND METHOD

(76) Inventors: Robert P. Carmichael, 17 Austin Terrace, Toronto, Ontario (CA), M5R 1Y2; George K. B. Sandor, 12 Hill Crescent, Toronto, Ontario (CA), M1M 1H9

( * ) Notice: Subject to any disclaimer, the term of this patent is extended or adjusted under 35 U.S.C. 154(b) by 80 days.

(21) Appl. No.: 10/086,859

(22) Filed: Mar. 4, 2002

(65) Prior Publication Data

US 2003/0165791 A1 Sep. 4, 2003

(51) Int. Cl.[7] ............................. A61C 3/02; A61C 8/00
(52) U.S. Cl. ......................................... 433/76; 433/173
(58) Field of Search ............................. 433/76, 72, 75, 433/173

(56) References Cited

U.S. PATENT DOCUMENTS

| | | | | |
|---|---|---|---|---|
| 4,568,285 A | * | 2/1986 | Chiaramonte et al. | 433/173 |
| 4,998,881 A | * | 3/1991 | Lauks | 433/173 |
| 5,320,529 A | * | 6/1994 | Pompa | 433/76 |
| 5,800,168 A | * | 9/1998 | Cascione et al. | 433/75 |
| 5,842,859 A | * | 12/1998 | Palacci | 433/72 |

FOREIGN PATENT DOCUMENTS

| EP | 1 084 682 A2 | 3/2001 |
|---|---|---|
| WO | WO 97/49351 | 12/1997 |

* cited by examiner

Primary Examiner—John J Wilson
(74) Attorney, Agent, or Firm—Bereskin & Parr

(57) ABSTRACT

The invention includes a method and apparatus to guide a dental drill to drill a bore into which a dental implant may be inserted at a particular axis. The dentist first takes an impression of a selected patient's dental arch. The cast dental arch is then formed from the impression. A dental professional then determines the desired location of the desired axis. A proxy implant having a proxy axis is placed in the cast dental arch with the proxy axis co-incident with the desired location of the desired axis. A stent is then formed of the tooth crowns from the cast dental arch. The stent has incorporated into it a locating barrel. A drill head with a drill alignment arm is provided to the dentist for fixation to a dental drill hand piece. The kit of parts provided to the dentist includes the stent with its incorporated locating barrel. The drill alignment arm provided to the dentist for attachment to the drill head and a plurality of drills. By using the stent with its incorporated locating barrel, the dentist's drill is guided into the desired location by interaction of the pin of the drill alignment arm with the locating barrel in the stent. By additionally controlling the length of the drills, the location, axis and depth of the drill hole made by the dentist will exactly coincide with the designed location, depth and orientation of the implant.

18 Claims, 10 Drawing Sheets

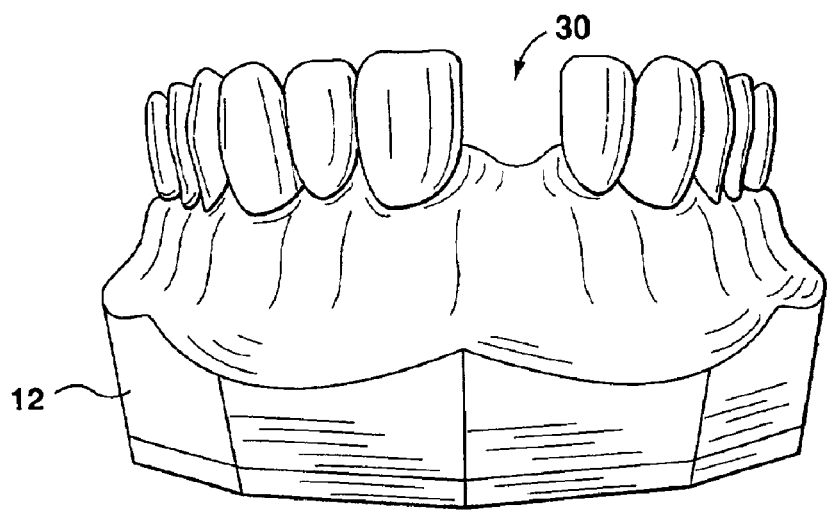
FIG. 2.1
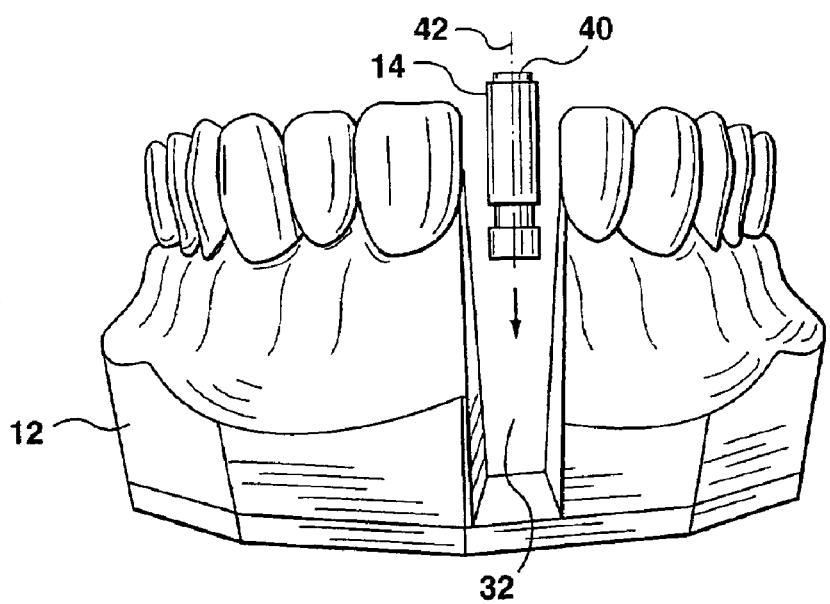
FIG. 2.2
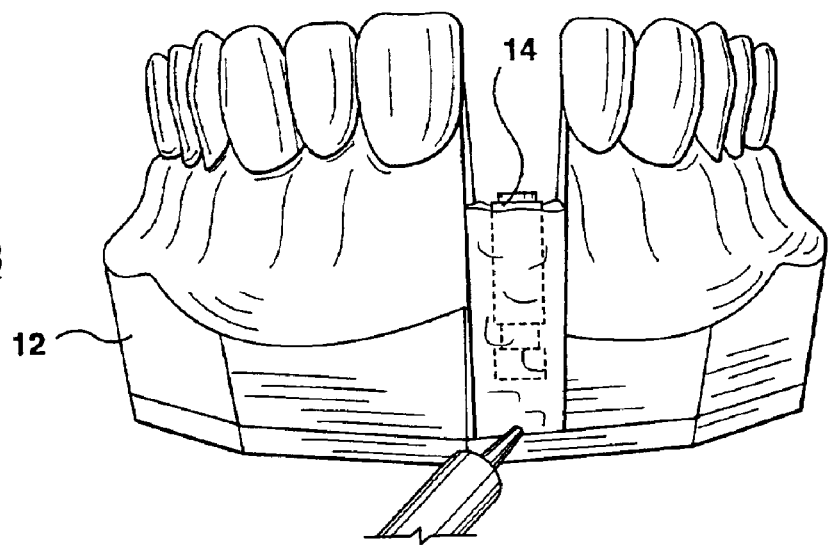
FIG. 2.3

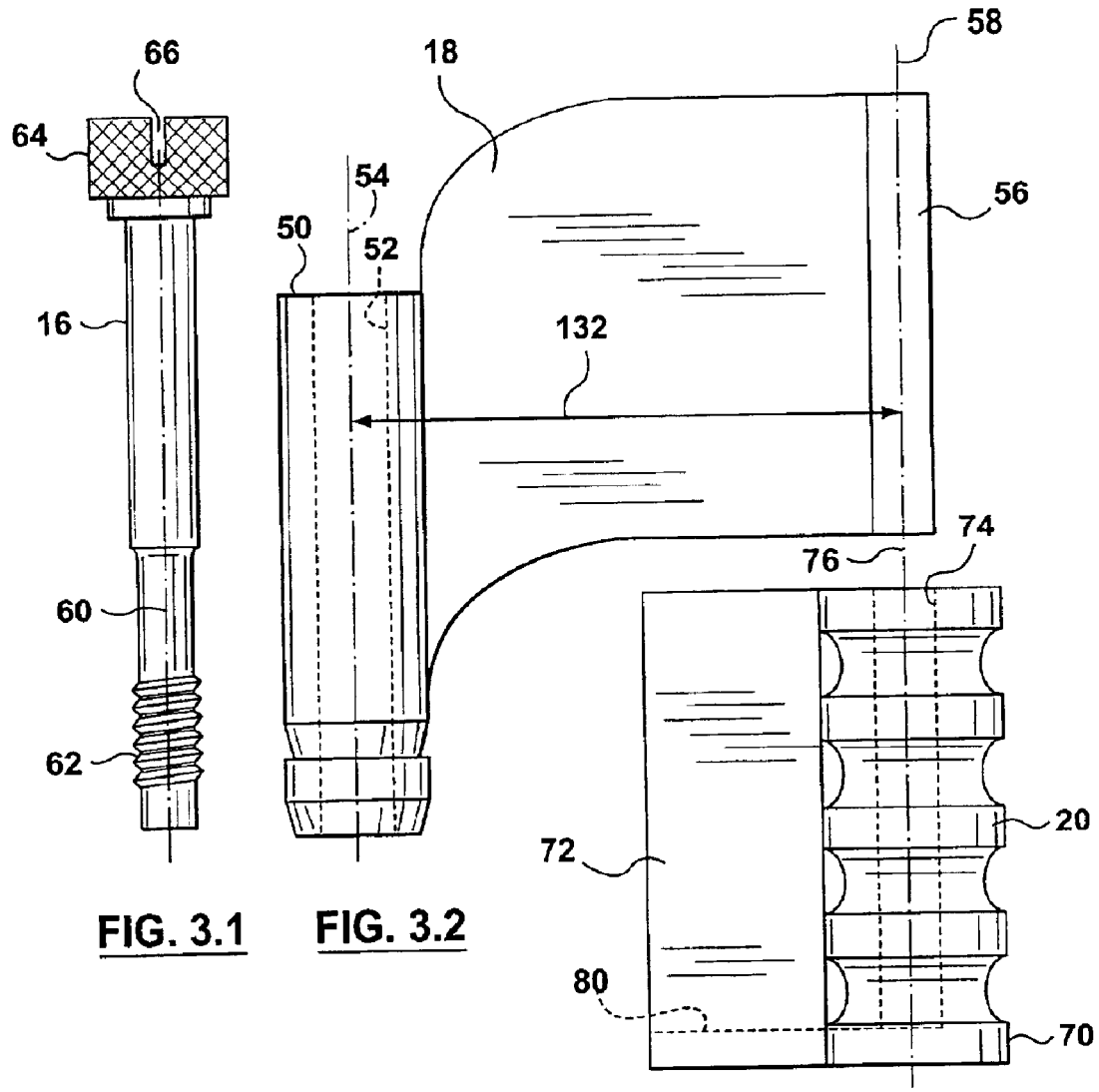
FIG. 3.1  FIG. 3.2
FIG. 3.3
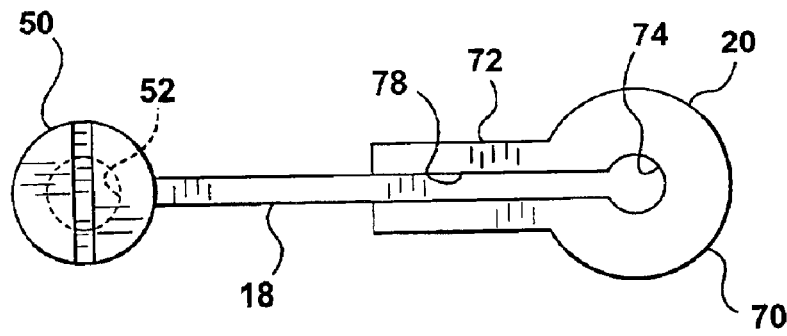
FIG. 3.4

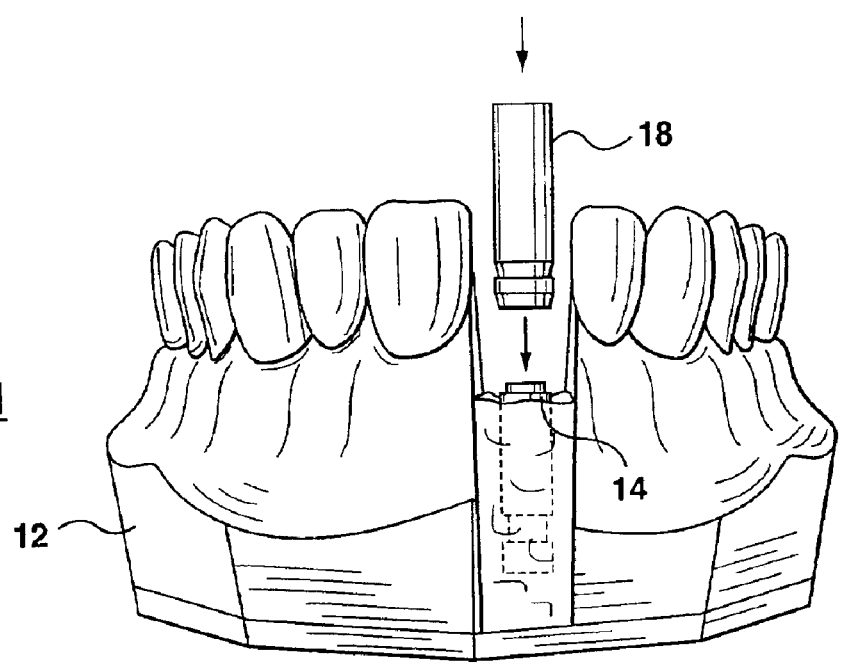
FIG. 4.1
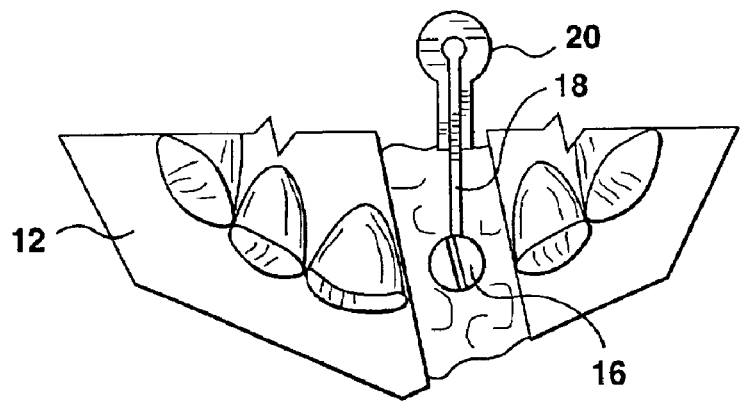
FIG. 4.2
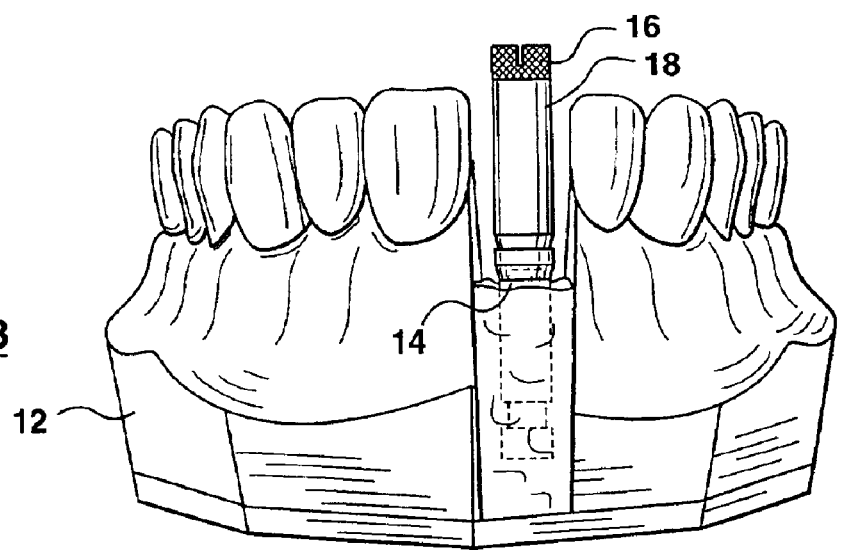
FIG. 4.3

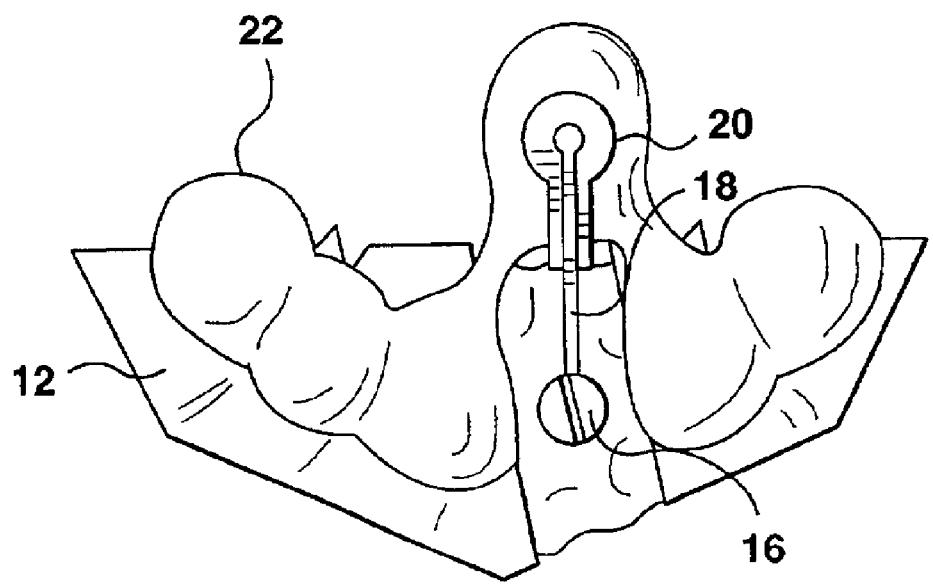
FIG. 5.1
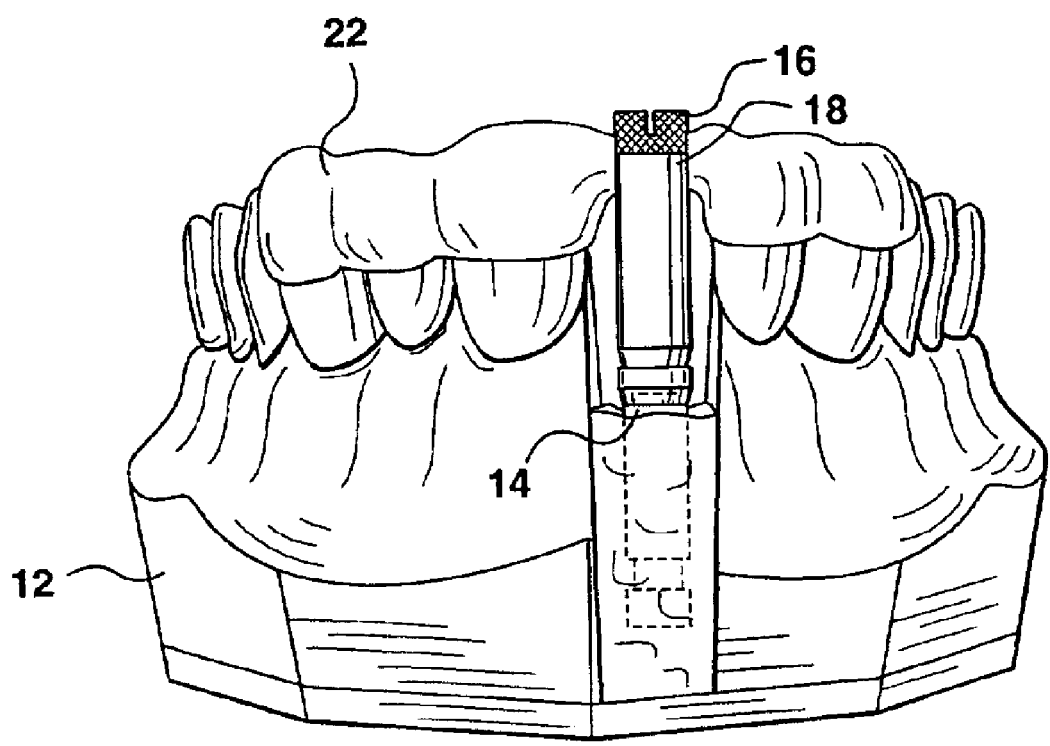
FIG. 5.2

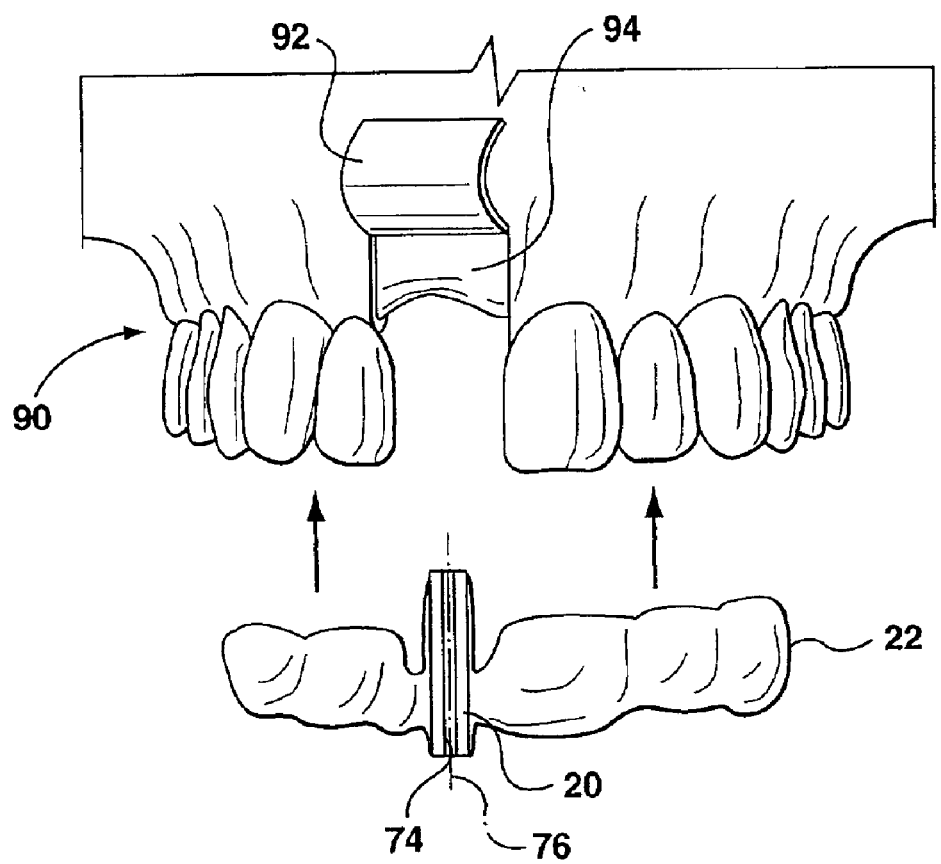
FIG. 7.1
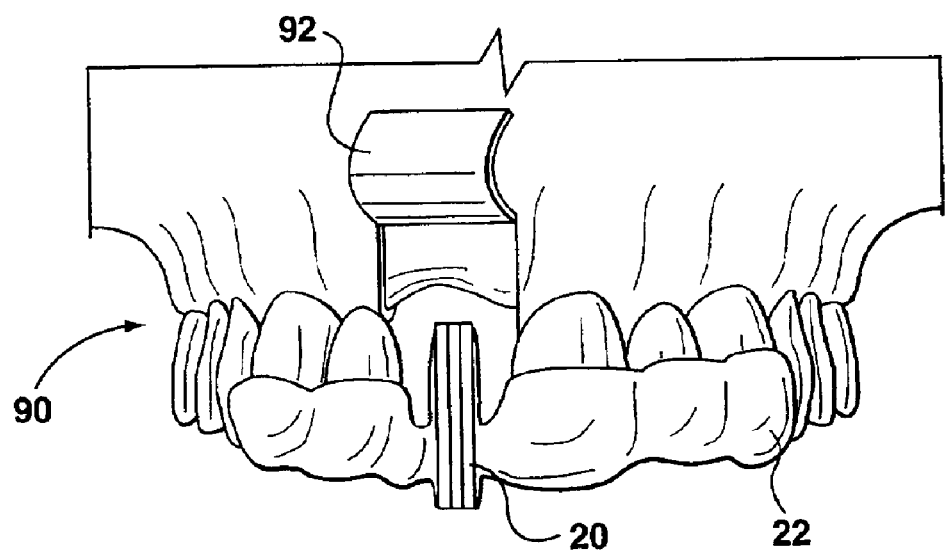
FIG. 7.2

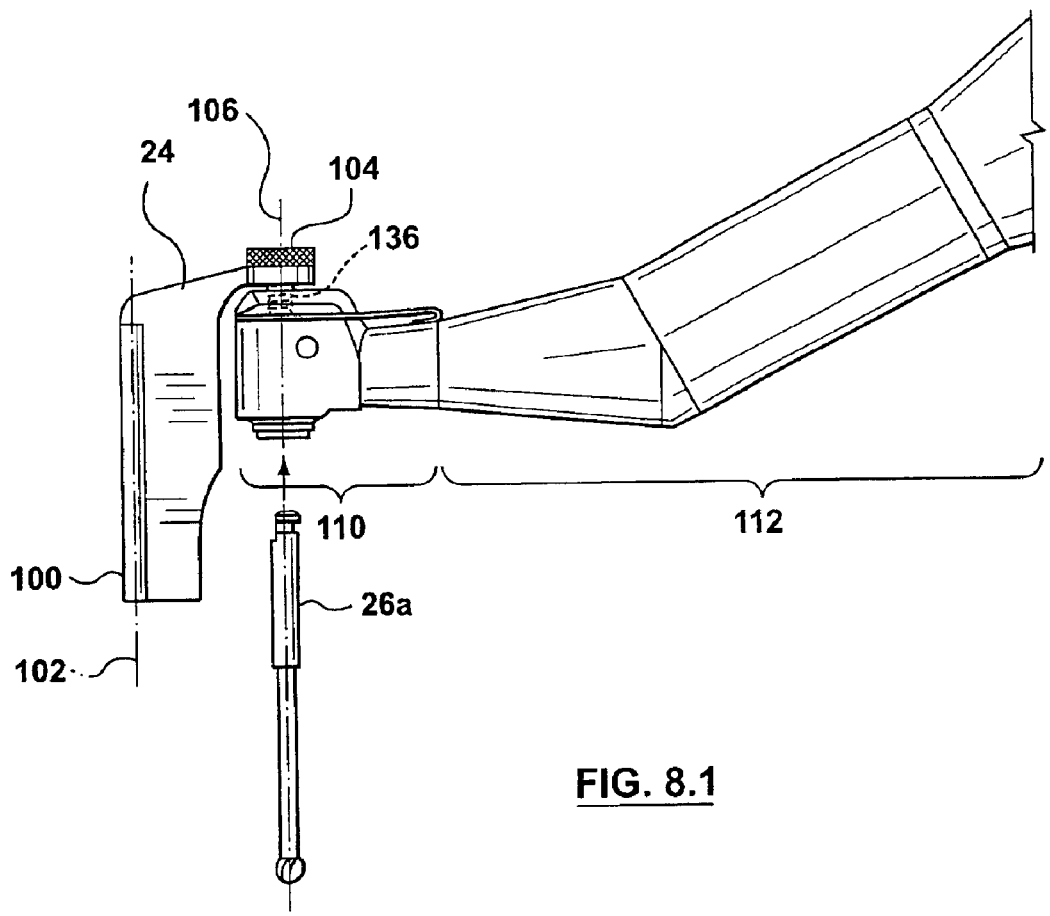
FIG. 8.1
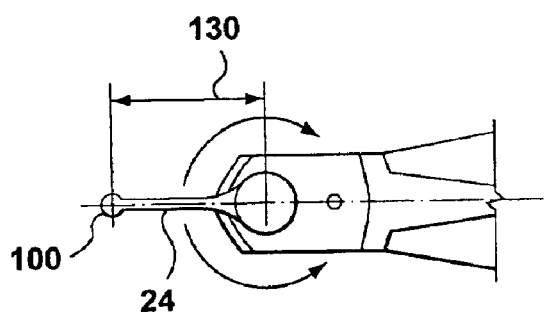
FIG. 8.2

IMPLANT POSITIONING DEVICE AND METHOD

FIELD OF THE INVENTION

This invention relates to the field of dentistry. In particular, the invention relates to the positioning of dental implants.

BACKGROUND OF THE INVENTION

Dental implants are commonly use in dental procedures. Often when a tooth has been removed, an implant is placed in the jaw bone and a dental prosthesis is then positioned using the implant. The implant is incorporated in the bone material and provides a suitable anchor for various types of dental prostheses.

Typically, when a dental implant is to be installed, a dentist prepares a cast of the patient's dental arch. That cast is then forwarded to a dental lab for creation of a suitable template. When the lab has determined the appropriate implant location to be used given the conditions of the patient's dental arch, the lab forwards a suitable template to the dentist. The dentist, guided by the template, installs the implant.

One of the problems that can arise in this situation is that the template provides only a rough or imprecise guide as to where the dentisit should place the implant. Practically speaking, the dentist is allowed considerable leeway in selecting the final position of the implant when using a template. Thus, because the dentist is given some leeway in deciding where the implant is to be placed, the location of the implant is not controlled and may not reflect the position intended by the laboratory. The error in location may be in several different directions. The implant may be positioned either left or right or forward or aft of the location expected by the lab. Also the location of the axis of the implant may be at an angle to that originally considered by the lab. Finally, the depth of the implant in the bone is also controlled by the dentist. All of these locations may vary from that originally intended by the lab. Accordingly, the design of the prosthesis may be non-ideal in terms of strength, esthetic appearance or the biological response it provokes.

Accordingly, it would be advantageous to provide a system which would provide better correlation between the intended location of a dental implant and the location at which the dental implant is installed by the dentist.

SUMMARY OF THE INVENTION

In accordance with one aspect of the invention, the invention includes a kit of parts. The kit of parts is used for aligning a drill axis of a dental drill head at a desired location in a selected patient's dental arch. The kit includes the drill alignment arm for attaching to a dental drill head at a specified drill head location. The drill alignment arm has a drill alignment arm pin and the drill alignment arm pin has a drill alignment arm pin axis. The kit further includes a stent which is adapted to fit the dental arch of a selected patient. The stent includes a locating barrel. The locating barrel has a bore adapted to receive and locate the drill alignment arm pin.

In a preferred embodiment, the locating barrel includes a depth control surface. In a further preferred embodiment of the invention, the kit includes at least one drill and the drill may have a length which is correlated with the depth control surface so that the drill may be used to drill a bore hole to a desired depth. Advantageously, the kit includes a plurality of drills having different diameters so a progressively larger hole may be drilled.

Additionally the kit may include a stent alignment arm. The stent alignment arm has a stent alignment arm pin and the stent alignment arm pin has a stent alignment arm pin axis. The stent alignment arm pin is adapted to be received within the bore of the locating barrel.

In a further preferred embodiment of the invention, the kit additionally includes proxy implant and the proxy implant has a central bore with a proxy axis.

In a further preferred embodiment the stent alignment arm includes an alignment coping and the alignment coping has an alignment coping bore with an alignment coping bore axis.

In a further preferred embodiment of the invention, the kit further includes a retainer screw for fixedly aligning the alignment coping of the stent alignment arm relative to the proxy implant with the alignment coping bore axis aligned with the proxy axis.

In accordance with another aspect of the invention, the invention includes a method of creating an alignment device for guiding a dental drill head for drilling a bore having a desired axis in a desired location with respect to a selected patient's dental arch. The method includes the steps of taking an impression of the selected patient's dental arch, forming a cast dental arch from the impression, determining the desired location of the desired axis and placing a proxy implant having a proxy axis in the desired dental arch so that the proxy axis is coincident with the desired location of the desired axis. The method further includes forming a stent of the selected patient's tooth crowns from the cast dental arch. The method further includes incorporating into the stent a locating barrel which has a locating barrel axis so that the locating barrel axis is spaced from the proxy axis by a first selected distance. The method also includes providing a drill alignment arm with the drill alignment arm having fixing means for fixing the drill alignment arm to the dental drill head at a predetermined location. The dental drill head has a drill axis. The drill alignment arm has a drill alignment arm pin having a drill alignment arm pin axis. The method further includes providing such parts wherein the drill alignment arm pin is spaced from the drill axis by a second selected distance and the first and second distances are equal.

DETAILED DESCRIPTION OF THE DRAWINGS

FIG. 1 illustrates the kit of parts which form a preferred embodiment of the invention and which may be used to practise a preferred embodiment of the method of the invention;

FIG. 2.1 is an enlarged version of a first component of the kit of FIG. 1;

FIG. 2.2 is a view similar to FIG. 2.1 but illustrating the placement of a second component of FIG. 1;

FIG. 2.3 illustrates the incorporation of the component shown in FIG. 2.2 in the component of FIG. 2.1;

FIG. 3.1 is an enlarged view of a third component of the kit of FIG. 1;

FIG. 3.2 is an enlarged view of a fourth component of the kit of FIG. 1;

FIG. 3.3 is an elevational view of a fifth component of the kit of FIG. 1;

FIG. 3.4 is a plan view of an assembly of the components of FIGS. 3.2 and 3.3;

FIG. 4.1 is an elevational view illustrating the assembly of the components of FIGS. 3.2 and 3.3 with the assembly as shown in FIG. 3.4;

FIG. 4.2 is a plan view of the completed assembly of the components illustrated in FIG. 4.1;

FIG. 4.3 is an elevational view of the assembly of FIG. 4.2;

FIG. 5.1 is a plan view of the assembly of FIG. 4.3 together with a sixth component of the kit of FIG. 1;

FIG. 5.2 is an elevational view of the assembly of components illustrated in FIG. 5.1;

FIG. 6 is an exploded elevational view showing the disassembly of components of FIG. 5.2;

FIG. 7.1 is an elevational view illustrating the alignment of one of the components of FIG. 1 on a patient;

FIG. 7.2 is an elevational view similar to FIG. 2.1 illustrating the completed placing of components illustrated in FIG. 7.1;

FIG. 8.1 is an elevational view illustrating a seventh component of FIG. 1 attached to a dental drill hand piece;

FIG. 8.2 is a plan view of the assembly of FIG. 8.1;

DETAILED DESCRIPTION OF THE INVENTION

Figure 1:
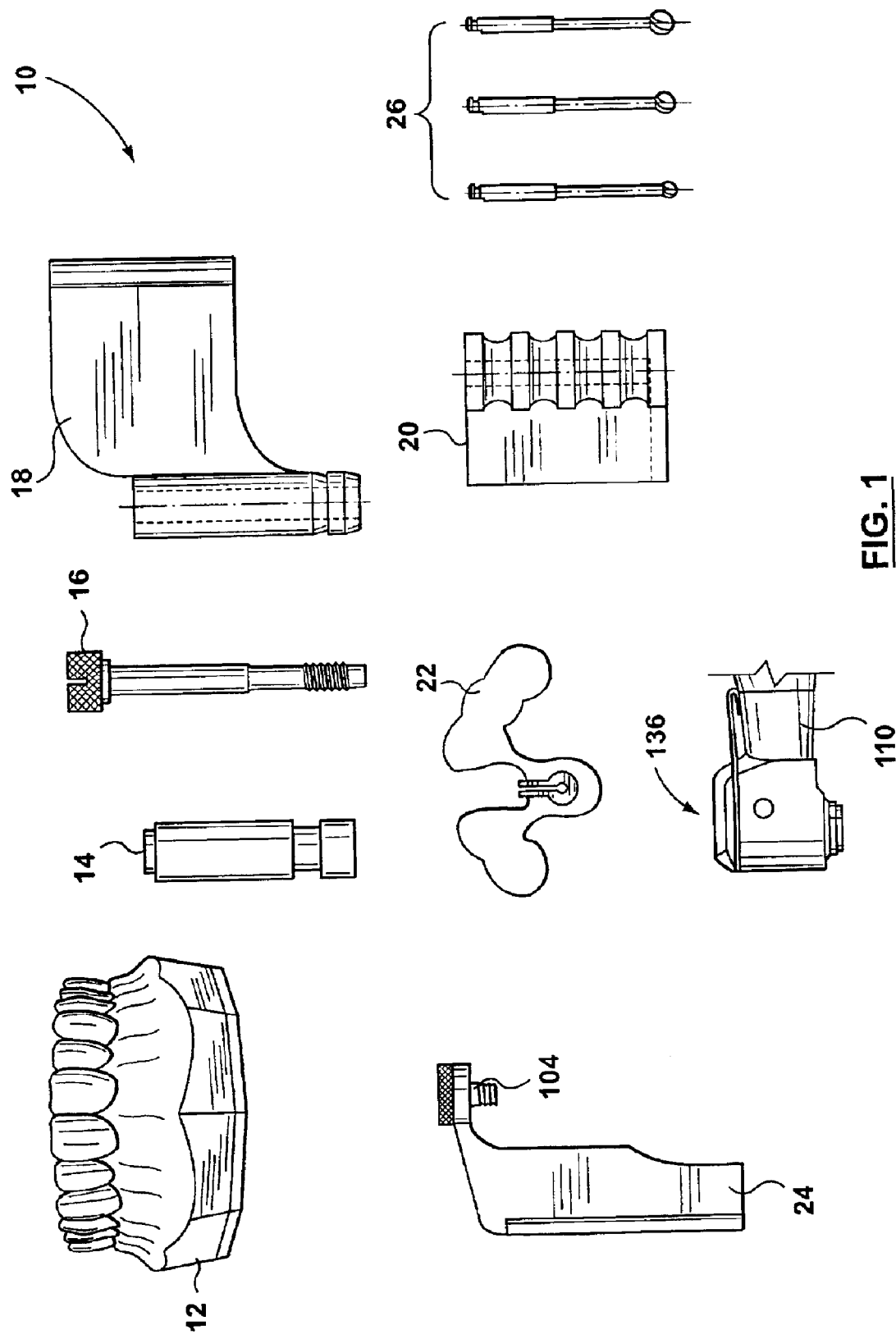

FIG. 1 illustrates a kit of parts that is useful in carrying out the method in accordance with a preferred embodiment of the invention. The kit of parts is indicated generally at 10. The kit includes a cast dental arch 12, a proxy implant 14, a retainer screw 16, a stent alignment arm 18, a locating barrel 20, a stent 22, a drill alignment arm 24 and a plurality of drills 26. The kit is used with a custom drill head 110 which may be part of the kit or dealt with separately.

The kit of parts 10 includes all the pieces required to use the invention described herein in accordance with the preferred embodiment. The persons involved in using the invention include the dental professional, the support staff in the dental professionals' office, dental laboratory professionals and support staff and manufacturers of the components of the kit of parts. Not all parts need be formed, manufactured or used by all persons involved. However, the kit illustrates all components which are used as explained below to establish installation of a dental implant in the place in the patient's jaw where intended by everyone involved in the patient's dental care.

In order to custom configure a dental implant to a patient, an impression is taken of the patient's dental arch. The dental arch may be either of the upper jaw or the lower jaw as required. The impression taken from the patient's dental arch will enable a cast dental arch to be made from the impression which duplicates the patient's dental arch. In most cases the cast dental arch will be made by the dentist from the impression made by the dentist. Either the impression or the cast dental arch, as appropriate, made by the dentist, is shipped to a laboratory facility. The cast dental arch will thus have the location of the patient's crowns, gums and bone structure. In addition, the cast dental arch made from the impression will duplicate the location of any gaps where teeth are missing and indicate the location where ultimately the implant is to be positioned in order to position a dental prosthesis.

Figure 10:
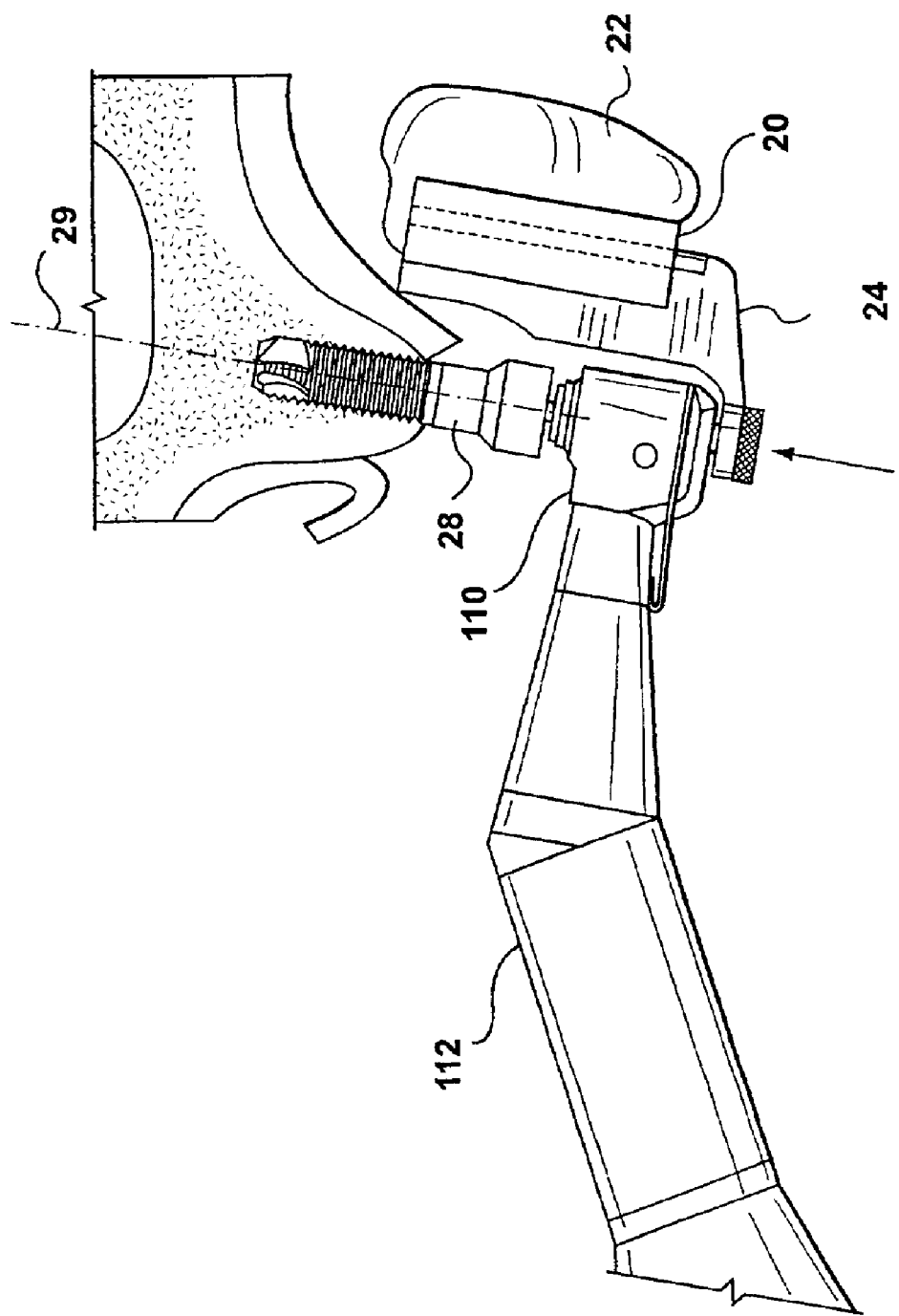
FIG. 10 is an elevational view illustrating the installation of a dental implant.

Upon receipt of the impression made by the dentist, the lab or other facility can then create a cast dental arch 12 from the impression which duplicates the patient's dental arch. Such a cast dental arch is illustrated in FIG. 2.1. From reference to FIG. 2.1, for convenience, there is illustrated a missing tooth at the maxiallary right central incisor position. The dental adviser to the patient has determined that a dental implant is required at that location. The site has been indicated generally by the arrow 30. The cast dental arch may be made from any material which is suitably rigid. At the intended site 30 where the implant 28 (see FIG. 10) is to be installed, the laboratory professional at the lab creates an excavated site 32 (see FIG. 2.2).

The next step in the procedure is to position the proxy implant 14 in a location determined by the dentist and laboratory professional. The proxy implant 14 is a proxy for the dental implant 28. The proxy implant 14 is located so that the location of the proxy implant will be suitable for integration of the dental implant 28 within the patient's bone structure so as to provide a suitable basis for a prosthesis. The proxy implant 14 comprises a central threaded bore 40. The central threaded bore 40 defines a proxy axis 42. The axis 42 will ultimately determine the location of a similar implant axis 29 in the implant 28. Thus, when the proxy implant 14 which is a proxy for the implant 28 is positioned in the arch as shown in FIG. 2.3, the implant axis 29 of the implant will be ultimately determined by the location of the proxy axis 42 of the proxy implant. In addition, as well as locating the proxy axis 42 and thereby the implant axis 29 with respect to the patient's dental arch, the proximal depth of the dental implant 20 may also be determined by the location of the proxy implant. This depth locating function will be discussed below after discussing the other elements of the kit 10 illustrated in FIG. 1. As shown in FIG. 2.3, when the location of the proxy implant has been determined, the proxy implant 14 is held in that location and a hardenable material such as silicone is used to encase the proxy implant 14. The hardenable material then cures so that the proxy implant 14 is permanently located with respect to the cast dental arch 12.

If desired, the cast dental arch with the proxy implant could be sent back to the dental professional for checking and vertification that the position of the implant as selected in the laboratory is acceptable to the dental professional. The dental professional may, for example, wish to verify that the implant, if positioned like the proxy implant, will be positioned to meet the patient's requirement, that is, would not conflict with roots of adjacent teeth or other bony or vital structure within the patient's mouth.

The next step in the procedure is to make use of the stent alignment arm 18 (see FIG. 3.2). The stent alignment arm 18 comprises an alignment coping 50 having a central bore 52 and an alignment coping axis 54. The stent alignment arm 18 also comprises a stent alignment arm pin 56. The stent alignment arm pin 56 is a substantially cylindrical configuration having a pin axis 58. The axis 58 is co-planar and parallel to axis 54.

The stent alignment arm 18 may be made from any dimensionally accurate material and may be reusable. Thus, the stent alignment arm 18 may be made from metal or suitable hard plastics having the necessary dimensional accuracy. The stent alignment arm 18 is not intended to be placed in the patient's mouth and is used only in the lab. Thus, the part need not be sterilizable. The axis 54 of the alignment coping 50 defines the bore 52 passing axially through the alignment coping 50 of the stent alignment arm 18. The bore 52 of the alignment coping 50 has a diameter to closely receive the shank of the retainer screw 16 illustrated in FIG. 3.1. The retainer screw 16 has a general axis 60. The retainer screw has a thread 62 at one end and a head 64 having a socket or slot 66 for turning the head by means of a screwdriver. The length of the retainer screw 16 along the axis 60 is greater than the axial length of the alignment coping 50 along axis 54. This means that when the retainer screw 16 is placed within the bore 52 of the alignment coping 50, the threaded end 62 will project beyond the length of the alignment coping 50 when the head 64 bears against the uppermost surface of the alignment coping 50 as illustrated in FIGS. 3.2 and 3.1.

The kit 10 illustrated in FIG. 1 also includes a locating barrel 20. The locating barrel 20 comprises a cylindrical portion 70 and a wing portion 72. The cylindrical portion 70 of the locating barrel 20 has a substantially cylindrical central bore 74 which has substantially the same diameter as the cylindrical portion of the stent alignment arm pin 56 and a locating barrel axis 76. The wing portion 72 of the locating barrel 20 has a central slot 78 whose width is the same as the width of the stent alignment arm 18 in the direction transverse to the plane including axes 54 and 58. The slot 78 and the bore 74 do not pass completely through the locating barrel 20, but rather, end in a surface shown in dotted lines at 80 in FIG. 3.3.

The locating barrel is a single use component and will be incorporated in a stent that will be placed in the patient's mouth. Thus, the locating barrel 20 may be manufactured from a sterilizable material, but as it is a single use device, it is preferable to make the locating barrel from a sterilizable plastic rather than more expensive materials such as metals.

The next step in the method is to assemble various of the parts discussed thus far. The locating barrel 20 is slid on to the stent alignment arm 18. The stent alignment arm pin 56 is received within the bore 74 of the locating barrel 20, while a portion of the stent alignment arm 18 is received within the slot 78. The locating barrel 20 is then pushed onto the stent alignment arm 18 until the stent alignment arm 18 bottoms out against surface 80. The assembled condition of these two parts is illustrated in FIG. 3.4.

The next step in the procedure is to place the assembly of the stent alignment arm 18 and locating barrel 20 on the proxy implant 14 which has been integrated into the cast dental arch 12. This is accomplished by aligning the alignment coping 50 so that axis 54 coincides with axis 42 of the encapsulated proxy implant 14. The retainer screw 16 is then passed downwardly through the alignment coping 50 along the alignment barrel bore 52. When the threaded end 62 of the retainer screw 16 encounters the threaded bore 40 of the proxy implant 14, the retainer screw 16 is rotated by means of the socket or slot 66. The thread 62 is sufficiently long to engage with the threaded central bore 40. The threaded central bore 40 is deep enough, however, that the screw 16 can be rotated until the head 64 of the screw engages the upper surface of the locating barrel 50 and the lower surface of the locating barrel 50 engages the upper surface of the proxy implant 14 as shown in FIG. 4.3. The initial alignment stage is shown in FIG. 4.1. The assembly is shown in FIG. 4.2 in a plan view and FIG. 4.3 in an elevational view.

The next procedure then occurs in the dental laboratory facility. A stent 22 is fabricated on the crowns of the cast dental arch 12. The stent 22 incorporates a plurality of crowns and should include enough of the crowns taken from the cast dental arch 12 so as to determine an accurate location of the stent relative to the assembly of the proxy implant 14, retainer screw 16, stent alignment arm 18 and locating barrel 20. The stent 22 encompasses the cylindrical portion 70 and the wing portion 72 of the locating barrel 20 but does not otherwise engage with or encapsulate the stent alignment arm 18 nor the retainer screw 16. The stent 22 may be made from any suitable material such as polymethyl methacrylate resin, bearing in mind that the stent needs to be relatively precise and will ultimately be placed within the patient's mouth. Thus, the material should be sterilizable or at least otherwise suitable for brief placement in the patient's mouth. The stent 22 is then left to fully set or cure.

Figure 6:
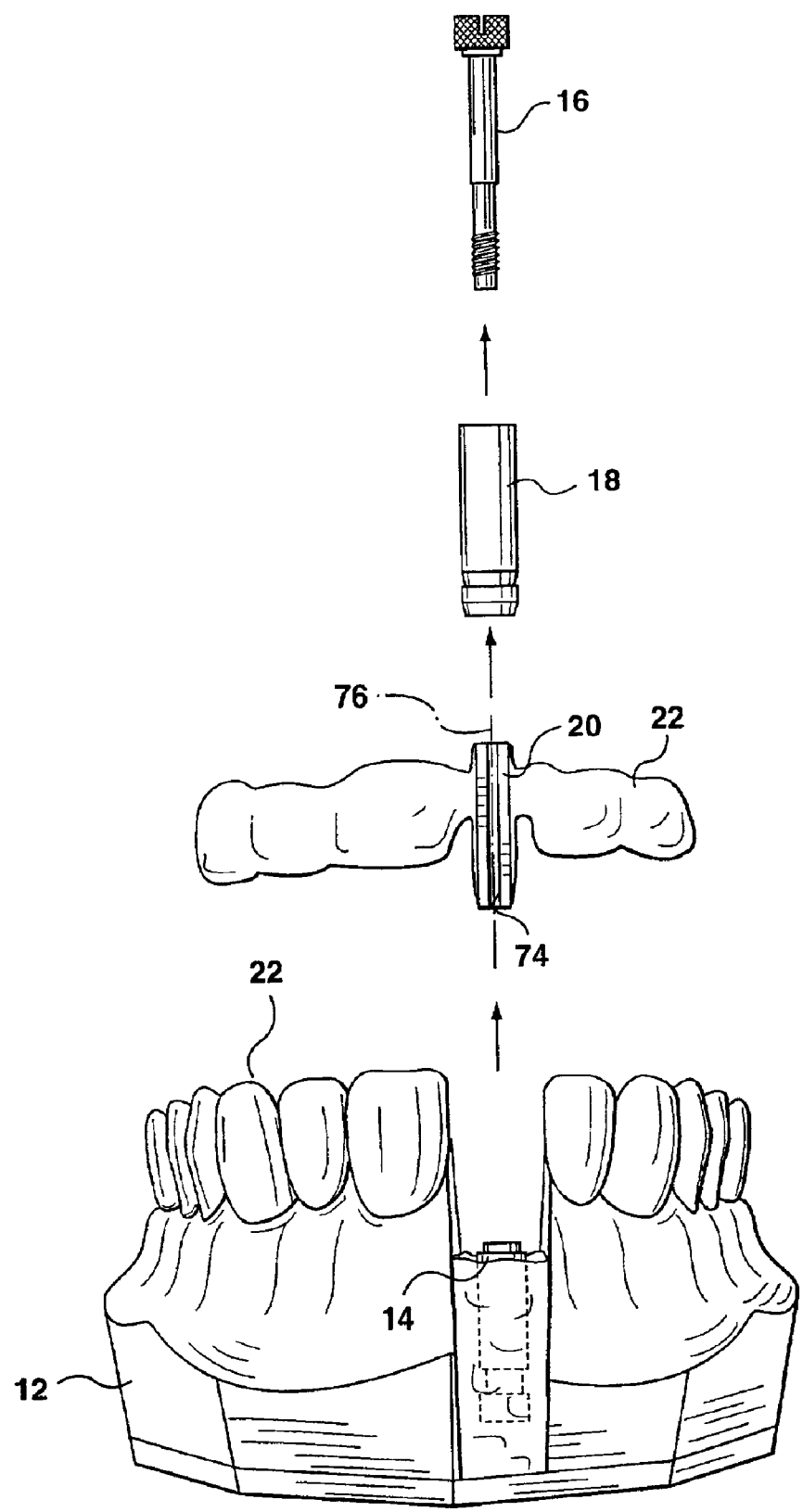
Figure 9:
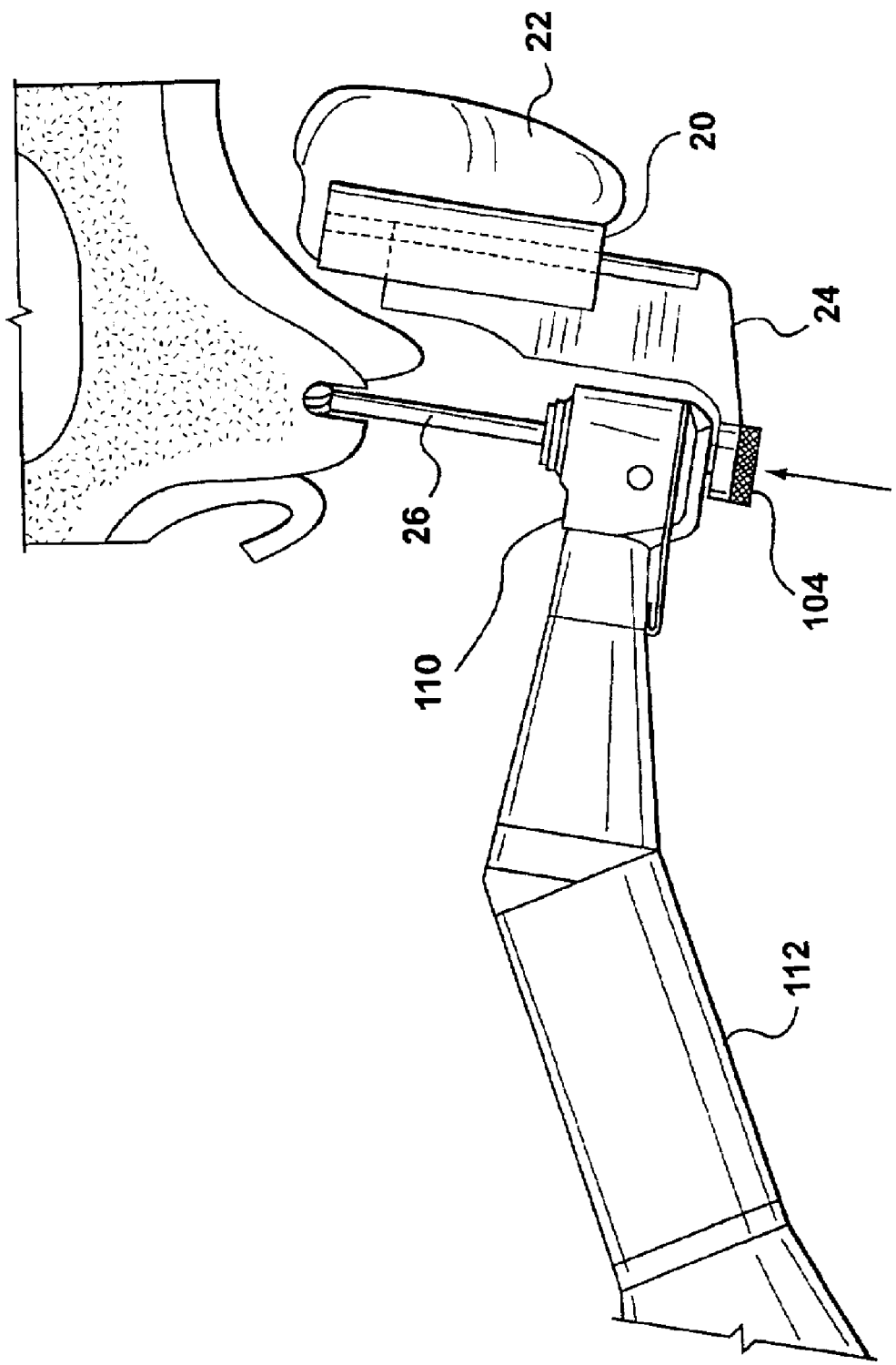
FIG. 9 is an elevational view illustrating the use of the components shown in FIG. 8.1 for drilling in a patient's mouth.

When the stent 22 has fully set or cured, it is disassembled from the cast dental arch 12. FIG. 6 illustrates an exploded elevational view showing the disassembly. The retainer screw 16 is unscrewed so that the threaded end 62 is released from the threaded central bore 40 of the proxy implant 14. The retainer screw can then be removed by being withdrawn upwardly as shown in FIG. 6. The removal of the retainer screw 16 thereby permits the removal of the stent alignment arm 18 from its position registering with the proxy implant 14. The stent alignment arm 18 can be removed from the stent 22 by sliding the stent alignment arm upwardly relative to the stent 22 as shown in FIG. 6. This then leaves an assembly of the stent 22 incorporating the locating barrel 20. The bore 74 and the locating barrel axis 76 of the locating barrel 20 is now located at a particular location and orientation relative to the proxy axis 42 of the proxy implant 14. No further use need be made of the cast dental arch 12 and the proxy implant 14 contained therein may be disposed of in due course. Because the proxy implant 14 is intended to be disposed of, that proxy implant may be made from aluminum or similar material.

It will also be appreciated that as the locating barrel 20 has a defined depth defined by the depth control surface 80, the surface 80 of the locating barrel when incorporated in the stent 22, creates a depth reference.

The dental professional who will install the implant 28 thus receives from the dental laboratory the stent 22 which has been processed to fit precisely on the patient's teeth. One or more drills 26 as necessary are used to create the appropriate site in the patient's mouth to incorporate the dental implant 28.

FIGS. 2.1 through 6.1 have all illustrated a cast of the dental arch placed on a flat surface such as a work bench in a position in which the crowns of the teeth face upwardly as displayed on the page and the references to up and down have been used in this description to designate directions relative to these figures. However, it will be recognized that this method and these components are equally useful whether it is the patient's upper dental arch or the lower dental arch that is to be the site of the dental implant. In FIGS. 7.1, 7.2, 9.1 and 10.1, the method and apparatus is illustrated installing a dental implant 28 in the patient's upper dental arch from whom the cast dental arch 12 illustrated in FIGS. 2 to 6 was made.

The first step will be for the dental professional to prepare the site for installation of the implant 28. The patient's dental arch is illustrated at 90 in FIG. 7.1. The site for the implantation of the dental implant 28 is made ready by removing soft tissue and exposing the bone. This is illustrated diagrammatically by a flap of soft tissue illustrated at 92 having been raised thereby exposing the bone 94. When the site is then ready for drilling a hole to accommodate the implant 28, the stent 22 is fitted to the patient's dental arch 90. Fitting the stent 22 to the patient's dental arch 90, positions the incorporated locating barrel 20 with precise reference to the patient's actual dental arch 90. The assembly of the stent 22 to the patient's dental arch 90 is illustrated in FIG. 7.2.

FIG. 8.1 illustrates a further component of the kit of FIG. 1. The drill alignment arm 24 comprises a drill alignment arm pin 100. The drill alignment arm pin 100 is a generally cylindrical structure having a drill alignment pin axis 102. The drill alignment arm 24 also includes an attachment screw 104. The drill alignment arm 24 is attached to the drill head 110 which is installed on a dentist's drill hand piece 112.

The drill head 110 accommodates a drill 26a illustrated in FIG. 8.1. FIG. 8.2 illustrates the assembly of the drill alignment arm 24 to the drill head 110 in plan view. The drill alignment arm 24 thus defines the relative location of a drill axis 106 of the drill 26a when mounted in the drill head 110 with respect to the axis 102 of the drill alignment arm pin 100. This relative distance is shown as 130 in FIG. 8.2. The distance 130 between the axes 102 and 106 is the same as the distance 132 between axes 54 and 58 of the stent alignment arm 18 (FIG. 3.3).

In order to begin the procedure of boring the hole into which the dental implant 28 will be received, the dental practitioner places the first drill 26a in the drill head 110. The drill 26a is then aligned in the correct position by sliding the drill alignment arm pin 100 with its axis 102 into the bore 74 of the locating barrel 20. This then aligns the axis 102 of the drill alignment arm pin 100 with the axis 76 of the locating barrel 20. Because the stent 22 accurately located the axis 76 relative to the axis 42 of the proxy implant 14, the axis 106 of the drill 26 is aligned with the location of the axis 42 of the proxy implant 14. Thus, the first drill 26a will drill a bore in the patient's bone 94 which is in exactly the same location as the axis 42 of the proxy implant 14, the intended axis of the installed implant 28. Depending upon the particular configuration of the implant 28, several drills 26 may be utilized to make a bore of suitable diameter in the patient's bone 94. Some implants have a threaded exterior surface and when that type of implant is desired, the final step in making the site in the bone may include the use of a tap to thread the bone to receive the implant.

As referred to above, the proximal height of the implant with respect to the patient's bone is also a critical component in determining the correct positioning of the implant. The depth of the bore in which the implant is to be installed is thus controlled by controlling the length of the drills provided to the dental practitioner for installing the implant. With drills of a predetermined length, the dentist aligns the drill head 110 by means of the stent 22 and its incorporated locating barrel 20 and advances the drill into the bone. The drill head 110 is then advanced proximally with respect to the host bone until the lower surface of the drill alignment arm 24 (as shown in FIG. 8.1) abuts the surface 80 of the locating barrel 20. Thus, the locating barrel 20 determines the location of the axis of the drill 106 and its angular orientation with reference to the crowns of the patient's dental arch and the length of the drill together with the surface 80 of the locating barrel determines the depth of the bore drilled into the patient's bone.

As discussed above, the kit preferably involves the use of a set of drills having the same length but of differing diameters so that the bone may be drilled to the desired size and depth. However, alternatively, to give more freedom of judgement to the dental professional who will be installing the implant, it would be desirable to supply alternate sets of drills. One set would have the length recommended by the dental laboratory; additional sets, however, may have a length greater than intially recommended or a length less than recommended. There may be additional sets with lengths considerably longer or shorter than recommended. This would facilitate the exercise of the skill and judgment of the dental professional. By way of example, the dental professional upon opening the patient's soft tissue, may find that the quantity of bone present at the desired location is different from what was expected and that the implant should be positioned somewhat higher or lower in the bone than originally planned.

In each set of drills, all drills would have the same length. Thus, once the dental professional decides the proper depth, a drill set is selected and then all bores drilled will have the same depth.

When the site for receiving the implant has been drilled and tapped as necessary, the dentist may then install the implant using the drill head 110 while the drill alignment arm 24 remains attached to the drill head 110. As the drill alignment arm pin 100 is passed into the locating barrel 20, the implant 28 is installed coaxially with the axis of the drills 26 which have been use to make the bore.

Once the implant has been installed, to the correct depth, the assembly of the drill head 110 and drill alignment arm 24 is removed from the stent 22. The stent 22 is then removed from the patient's teeth and the site of installation of the implant is closed to permit integration of the implant 28.

The above procedure and components thus ensure that the implant 28 is located precisely in the location determined from the patient's dental cast when studied by the dental professionals in the laboratory as shown in FIG. 2.2.

When the procedure has been completed, the drill alignment arm 24 may be removed from the drill head 110 so that the drill head 110 can be used for other purposes. The drill head 110 is similar to the drill head which a dentist may already possess which is adapted to be driven by the dentist's drill hand piece 112. The only adaption which is necessary is the modification which permits the drill alignment arm 24 to be attached to the drill head 110. Conveniently, the drill alignment arm 24 may be provided with a screw 104. To modify the drill head 110, a threaded bore 136 is provided. The bore 136 is threaded to accept the screw 104.

The drill head 110 attaches to the drill hand piece 112. There are several options for this component of the kit of parts. A standard drill head could be modified as discussed above. Alternatively, a single piece drill head and drill alignment arm can be produced. The principal maintained is the axis 106 of a drill inserted into the drill head is at a known distance from the axis 102 of the drill alignment arm pin.

While the terms "up" and "down" have been used in this description of a preferred embodiment, the axis of drilling may not be vertically up or down, but may be located at any orientation as desired to meet the patient's needs.

The present invention may be embodied in other specific forms without departing from the spirit or essential characteristics thereof. The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

We claim:

1. A kit of parts for aligning a drill axis of a dental drill head at a desired location in a selected patient's dental arch comprising:

a drill alignment arm for attaching to said dental drill head at a specified drill head location, said drill alignment arm having a drill alignment arm pin, said drill alignment arm pin having a drill alignment arm pin axis, and a stent, said stent adapted to fit said dental arch of said selected patient, said stent including a locating barrel, said locating barrel having a bore adapted to receive and locate said drill alignment arm pin, said locating barrel includes a depth control surface, said kit including at least one drill, said at least one drill having a selected drill length and said selected drill length and said depth control surface are correlated to limit the depth of a bore which may be drilled by said at least one drill when mounted in said drill head, to a desired depth, said kit further including a plurality of drills, said drills having different diameters, said kit including a dental implant and wherein one of said drills is adapted to drill a bore of a size to accommodate said implant, and wherein said kit further comprises a stent alignment arm, said stent alignment arm having a stent alignment arm pin, said stent alignment arm pin having a stent alignment arm pin axis, and said stent alignment arm pin, is adapted to be received within said bore of said locating barrel.

2. The kit of claim 1 wherein said kit comprises a proxy implant, said proxy implant having a central bore, said central bore having a proxy axis.

3. The kit of claim 2 wherein said stent alignment arm comprises an alignment coping, said alignment coping having an alignment coping bore with an alignment coping bore axis.

4. The kit of claim 3 wherein said kit further comprises a retainer screw for fixedly aligning said alignment coping of said stent alignment arm, relative to said proxy implant with said alignment coping bore axis aligned with said proxy axis.

5. The kit of claim 4 wherein the distance between said alignment coping bore axis and said stent alignment arm pin axis is the same as the distance between said drill alignment arm pin axis and said drill axis when said drill alignment arm is fixed to said drill head.

6. The kit of claim 5 wherein said locating barrel includes a slot portion for removably receiving a portion of said stent alignment arm when said stent alignment arm pin is received within said bore of said locating barrel.

7. The kit of claim 1 wherein said kit comprises a proxy implant, said proxy implant having a central bore, said central bore having a proxy axis.

8. The kit of claim 7 wherein said stent alignment arm comprises an alignment coping, said alignment coping having an alignment coping bore with an alignment coping bore axis.

9. The kit of claim 8 wherein said kit further comprises a retainer screw for fixedly aligning said alignment coping of said stent alignment arm, relative to said proxy implant with said alignment coping bore axis aligned with said proxy axis.

10. The kit of claim 9 wherein the distance between said alignment coping bore axis and said stent alignment arm pin axis is the same as the distance between said drill alignment arm pin axis and said drill axis when said drill alignment arm is fixed to said drill head.

11. The kit of claim 10 wherein said locating barrel includes a slot portion for removably receiving a portion of said stent alignment arm when said stent alignment arm pin is received within said bore of said locating barrel.

12. A method of creating an alignment device for guiding a dental drill head for drilling a bore having a desired axis in a desired location with respect to a selected patient's dental arch comprising the steps of:

taking an impression of said selected patient's dental arch, forming a cast dental arch from said impression, determining said desired location of said desired axis, placing a proxy implant having a proxy axis in said cast dental arch so that said proxy axis is coincident with said desired location of said desired axis, forming a stent of said selected patient's tooth crowns from said cast dental arch, incorporating into said stent, a locating barrel, said locating barrel having a locating barrel axis, so that said locating barrel axis is spaced from said proxy axis by a first selected distance, providing a drill alignment arm, said drill alignment arm, having fixing means for fixing said drill alignment arm to said dental drill head at a predetermined location, said dental drill head having a drill axis, said drill alignment arm having a drill alignment arm pin having a drill alignment arm pin axis, and wherein said drill alignment arm pin is spaced from said drill axis by a second selected distance, and wherein said second selected distance is equal to said first selected distance.

13. The method of claim 12 further including the step of providing a depth control surface in said locating barrel.

14. The method of claim 13 including the step of providing at least one drill for use in said drill head and determining the length of said at least one drill so that a bore to be drilled along said desired axis at said desired location will be limited in depth by the depth control surface of said locating barrel.

15. A method for creating an alignment device for guiding a dental drill head for drilling a bore having a desired axis at a desired location comprising, forming a cast dental arch from an impression made of a selected patient's mouth;

determining a desired location in said cast dental arch for installation of a dental implant, fixing a proxy implant in said cast dental arch at said desired location, fixing a stent alignment arm with respect to said proxy implant, said stent alignment arm including a stent alignment arm pin, placing a locating barrel on said stent alignment arm, so that said stent alignment arm pin is received within said locating barrel, providing a stent made from the crowns of said dental arch, and incorporating said locating barrel in said stent, providing a drill alignment arm, said drill alignment arm, having a drill alignment arm pin, said drill alignment arm pin being receivable within said bore of said locating barrel, and providing fixation means on said drill alignment arm, for fixing said drill alignment arm to said drill head at a particular location.

16. The method of claim 15 further comprising providing said stent and said drill alignment arm, to a dental professional for drilling a bore having said desired axis at said desired location in said selected patient.

17. The method of claim 16 including the step of providing to said dental professional, at least one drill, said at least one drill having a predetermined length.

18. The method of claim 17 comprising the additional step of providing a depth control surface in said locating barrel.

* * * * *